US005088495A

United States Patent [19]

Miyagawa

[11] Patent Number: 5,088,495

[45] Date of Patent: Feb. 18, 1992

[54] MECHANICAL ULTRASONIC SCANNER

[75] Inventor: Toyomi Miyagawa, Chigasaki, Japan

[73] Assignee: Kabushiki Kaisha Toshiba, Kawasaki, Japan

[21] Appl. No.: 472,880

[22] Filed: Jan. 31, 1990

[30] Foreign Application Priority Data

Mar. 27, 1989 [JP] Japan .................................. 1-71906
Sep. 20, 1989 [JP] Japan .................................. 1-241862

[51] Int. Cl.[5] .................................. A61B 8/00
[52] U.S. Cl. .................................. 128/660.1; 73/633
[58] Field of Search .................................. 128/660.09, 660.1; 73/629, 633, 640

[56] References Cited

U.S. PATENT DOCUMENTS

| | | | |
|---|---|---|---|
| 3,175,106 | 3/1965 | Sansom et al. | 310/336 |
| 3,800,276 | 3/1974 | Rishell | 367/149 |
| 3,968,459 | 7/1976 | Jacobson | 310/335 X |
| 4,377,088 | 3/1983 | Evert | 73/640 |
| 4,433,691 | 2/1984 | Bickman | 128/660.1 |
| 4,479,388 | 10/1984 | Matzuk | 128/660.1 X |
| 4,515,017 | 5/1985 | McConaghy et al. | 73/618 |
| 4,517,985 | 5/1985 | Teslawski et al. | 73/620 X |
| 4,531,412 | 7/1985 | Prud'hon et al. | 73/633 X |
| 4,622,501 | 11/1986 | Eventoff et al. | 73/620 |
| 4,671,292 | 6/1987 | Matzuk | 128/660.1 |
| 4,784,148 | 11/1988 | Dow et al. | 128/660.1 |

FOREIGN PATENT DOCUMENTS

| | | |
|---|---|---|
| 0191546 | 8/1986 | European Pat. Off. . |
| 3721183 | 1/1989 | Fed. Rep. of Germany . |

OTHER PUBLICATIONS

Ultrasonics, vol. 16, No. 4, Jul. 1978, Guildford GB, pp. 171-178, T. Matzuk et al., "Novel Ultrasonic Real--Time Scanner Featuring Servo Controlled Transducers Displaying a Sector Image".

Elektronik, May 17, 1985, Munchen DE, pp. 99-101, A Petersen, "Magnetoresistive Sensoren im Kfz".

*Primary Examiner*—Francis Jaworski
*Attorney, Agent, or Firm*—Oblon, Spivak, McClelland, Maier & Neustadt

[57] ABSTRACT

A mechanical ultrasonic scanner includes a transducer element which is swingably supported in a housing, and a sensor for detecting a swinging angle of the transducer element. The sensor includes a permanent magnet swung together with the transducer element, and a magnetoresistive element fixed to the housing to be opposite to a swinging locus of the permanent magnet. The permanent magnet generates a magnetic field between the permanent magnet and the magnetoresistive element. The magnetoresistive element detects a strength of the magnetic field which changes in correspondence with a swinging angle of the magnet, so that the swinging angle of the transducer element is detected on the basis of the change in the strength of the magnetic field. Even if the housing contains a sound transmitting medium, the magnetic field generated by the sensor is not adversely affected by the sound transmitting medium. Therefore, the swinging angle of the transducer element can be accurately detected to accurately obtain a radiating/returning direction of an ultrasonic beam, thus accurately reconstructing an image. In addition, the position of the transducer element can be controlled with high precision.

25 Claims, 18 Drawing Sheets

(OPEN SLOT SHAPE)

( OPEN SLOT SHAPE WITH TEETH )

MECHANICAL ULTRASONIC SCANNER

BACKGROUND OF THE INVENTION

1. Field of the Invention

The present invention relates to a mechanical ultrasonic scanner for mechanically swinging a transducer element, thereby scanning the interior of a living body by a ultrasonic beam emitted from the transducer element, so that an image of the structure and movement of internal organs of the living body is displayed in real time.

2. Description of the Related Art

In a mechanical ultrasonic scanner, a transducer element is swingably supported in a housing. This transducer element radiates an ultrasonic beam while being swung by, e.g., a motor. Therefore, the inside of a living body is scanned by the ultrasonic beam. After scanning, the ultrasonic beam returned from the living body is detected by the transducer element. The detected ultrasonic beam reconstructs an image to obtain a tomogram.

The housing contains a liquid sound transmitting medium (e.g., a mineral oil). The transducer element is dipped in the sound transmitting medium. This sound transmitting medium has a property of easily transmitting an ultrasonic beam in a frequency range incident on a living body. Therefore, the ultrasonic beam radiated from the transducer element can be transmitted without being obstructed in the housing, and can be incident on the living body.

In order to reconstruct an image by the detected ultrasonic beam, a direction in which the ultrasonic beam is radiated and returned from/to the transducer element must be detected. Therefore, a swinging angle of the transducer element is conventionally detected by an optical encoder to obtain a radiating/returning direction of the ultrasonic beam.

In a liquid sound transmitting medium, however, light emitted from the optical encoder may be irregularly reflected. In addition, swinging of the transducer element causes the sound transmitting medium to flow, and irregular reflection of the light is enhanced. Furthermore, straight propagation of the light may often be interrupted by dust which floats in the sound transmitting medium. For these reasons, the light is not accurately detected, and the swinging angle of the transducer element is not often detected accurately. Therefore, a radiating/returning direction of the ultrasonic beam cannot be accurately obtained, and a reconstructed image may often be inaccurate.

SUMMARY OF THE INVENTION

It is an object of the present invention to provide a mechanical ultrasonic scanner for accurately detecting a swinging angle of a transducer element to accurately obtain a radiating/returning direction of an ultrasonic beam, thus accurately reconstructing an image.

According to the present invention, there is provided a mechanical ultrasonic scanner, comprising:

a housing;

a transducer element arranged in said housing;

means for swinging said transducer element; and means for detecting a swinging angle of said transducer element, said detecting means including a first member which is swung together with said transducer element, and a second member attached to said housing to be opposite to a part of a swinging locus of the first member, said detecting means causing one of the first and second members to generate a magnetic field between them, causing the other of the first and second members to detect a strength of the magnetic field which changes in correspondence with a swinging angle of the first member, and detecting the swinging angle of said transducer element on the basis of the change in strength of the detected magnetic field.

In the present invention, a swinging angle of the transducer element is detected by a magnetic detecting means. For this reason, even if he housing contains a sound transmitting medium, a magnetic field radiated from the detecting means is not adversely affected by the sound transmitting medium. Therefore, in the present invention, the swinging angle of the transducer element can be accurately detected to accurately obtain a radiating/returning direction of the ultrasonic beam, thus accurately reconstructing an image. In addition, the position of the transducer element can be controlled with high precision.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 3:
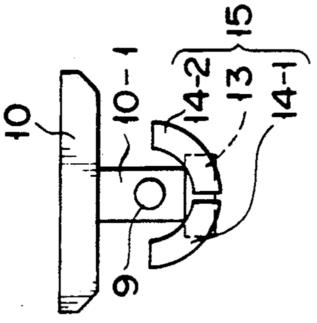
FIG. 3 is a front view of a sensor for detecting a swinging angle of a transducer element arranged in the ultrasonic scanner shown in FIGS. 1 and 2.
Figure 4:
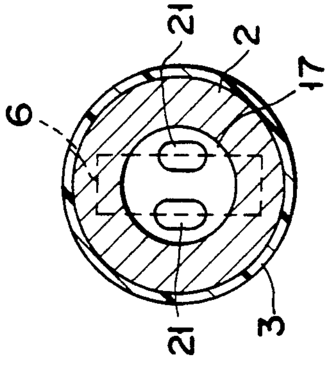
FIG. 4 is a sectional view taken along the line of IV—IV of FIG. 2.
Figure 2:
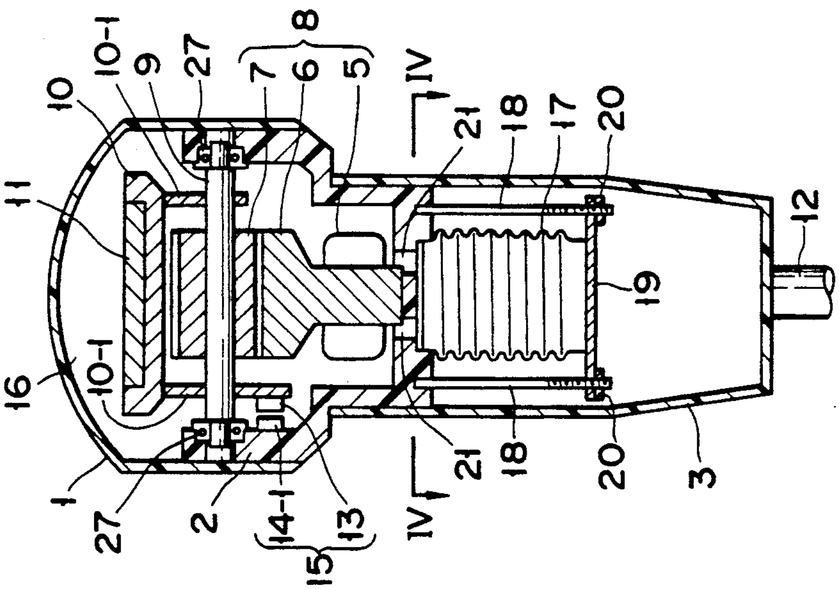
FIG. 2 is a side sectional view of the ultrasonic scanner shown in FIG. 1.

FIGS. 1 to 4 show a mechanical ultrasonic scanner according to the first embodiment of the present invention. This scanner includes a housing 4. The housing 4 includes a spherical shell-like cap 1 through which an ultrasonic beam is transmitted, a shielding case 2 to which the cap 1 is fixed, and a holding case 3 for supporting the shielding case 2.

A chamber 16 defined by the cap 1 and the shielding case 2 contains a sound transmitting medium. In addition, a transducer element 11 and a swinging motor 8 for swinging the transducer element 11 are arranged in the chamber 16. More specifically, the transducer element 11 is supported by a support member 10, and an extending member 10-1 which extends from the support member 10 is fixed to a rotating shaft 9 rotatably supported by bearings 27 of the shielding case 2.

The swinging motor 8 includes a stator 6 fixed to the shielding case 2, an exciting coil 5 wound around the stator 6, and a rotor 7 which is disposed between a pair of opposite surfaces 6-1 and 6-2, and is fixed to the rotating shaft 9. The stator 6 is made of, e.g., a soft magnetic iron (SUSYB material), a rolled steel for general structure (SS41), or silicon steel (S-10). The rotor 7 is made of a permanent magnet having north and south poles polarized by a plane including the center of the rotating shaft 9.

In the swinging motor 8, when a current is periodically supplied to the exciting coil 5, a pair of opposite surfaces 6-1 and 6-2 of the stator 6 are periodically excited. As a result, the pair of opposite surfaces 6-1 and 6-2 are periodically magnetized to the north and south poles to swing the rotor 7 and the rotating shaft 9.

An operation of the swinging motor 8 will be described below in detail with reference to FIGS. 5A to 5E.

Figures 5A, 5B, 5C:
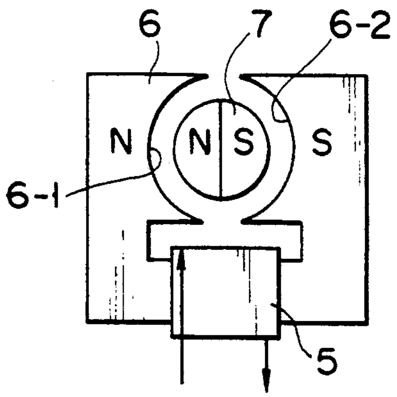
FIGS. 5A to 5E are schematic views for explaining an operation of a swinging motor.

Referring to FIG. 5A, when a current is supplied to the exciting coil 5 in a direction indicated by an arrow, the pair of opposite surfaces (magnetic poles) 6-1 and 6-2 are magnetized to the north and south poles, respectively. The rotor (permanent magnet) 7 is opposite to the magnetic poles in the manner of N—N, and S —S, and a direction of a magnetomotive force of an armature coincides with that of a permanent magnet. Therefore, an attractive force between the permanent magnet and the magnetic poles is set to be "0" (cogging torque).

FIG. 5B shows a case wherein the permanent magnet is rotated clockwise by 45°. Since the direction of the magnetomotive force of the armature has a phase difference of 45° from that of the permanent magnet, a clockwise torque is generated by the vertical components thereof. However, since the magnetic center of the magnetomotive force of the permanent magnet is shifted from that of the north magnetic pole by 45°, a torque in a direction to match the magnetic centers, i.e., a counterclockwise torque is also generated. As a result, a rotational torque is generated in a direction obtained by synthesizing the clockwise and counterclockwise rotational torques.

In FIG. 5C, since the direction of the magnetomotive force of the armature is perpendicular to that of the permanent magnet, a maximum clockwise torque can be obtained. Since the magnetic center of the permanent magnet is shifted from that of the magnetic poles by 90°, a force between the permanent magnet and the magnetic pole is set to be "0". Therefore, the synthetic torque includes only a torque generated by the magnetomotive force of the armature.

Figures 5D, 5E:
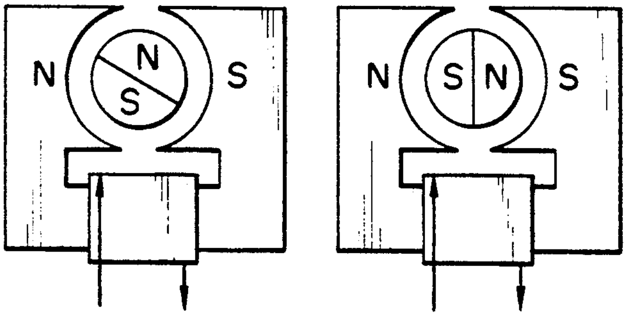

FIG. 5D shows a case wherein the permanent magnet is further rotated clockwise by 45°. Since the direction of the magnetomotive force of the armature is shifted from that of the permanent magnet by 45° as in FIG. 5B, a clockwise torque is generated by the vertical components thereof. However, since the magnetic center of the magnetomotive force of the permanent magnet is shifted from that of the south magnetic pole by 45°, a torque in the direction to match the magnetic centers, i.e., a clockwise torque is also generated. As a result, a rotational torque is generated in the direction obtained by synthesizing the clockwise and counterclockwise rotational torques.

In FIG. 5E, the permanent magnet is opposite to the magnetic poles in the manner of N—S, and S—N, unlike in FIG. 5A, and the direction of the magnetomotive force of the armature coincides with that of the permanent magnet. A torque is not generated by excitation of the armature, and the magnetic center of the direction of the magnetomotive force of the permanent magnet also coincides with that of the magnetic poles. Therefore, a cogging torque is set to be "0".

When the permanent magnet is set in the state shown in FIG. 5E, and the direction of a current supplied to the exciting coil 5 is reversed, a torque in the opposite direction can be obtained. Therefore, the swinging motor 8 can swing the rotor (permanent magnet) 7.

Figure 6:
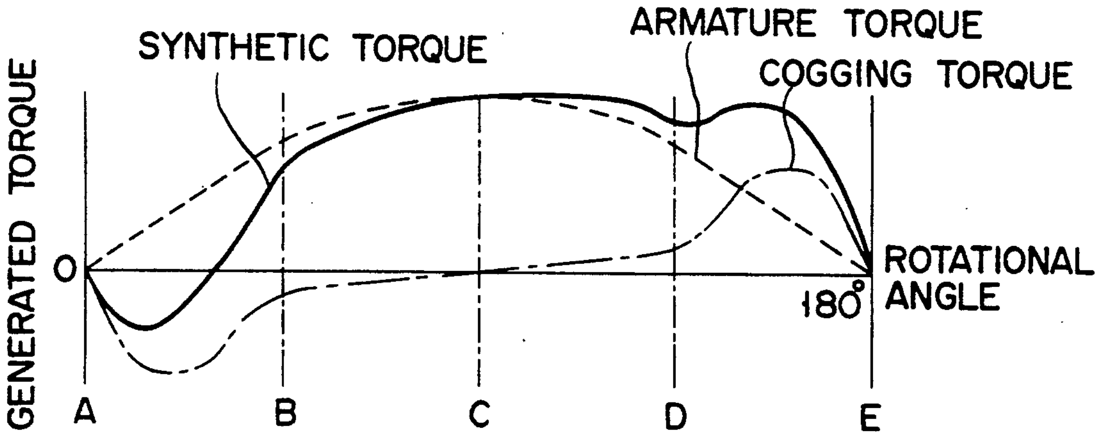
FIG. 6 is a graph showing a relationship between a torque generated from the swinging motor and a rotational angle of a rotor.
Figure 7:
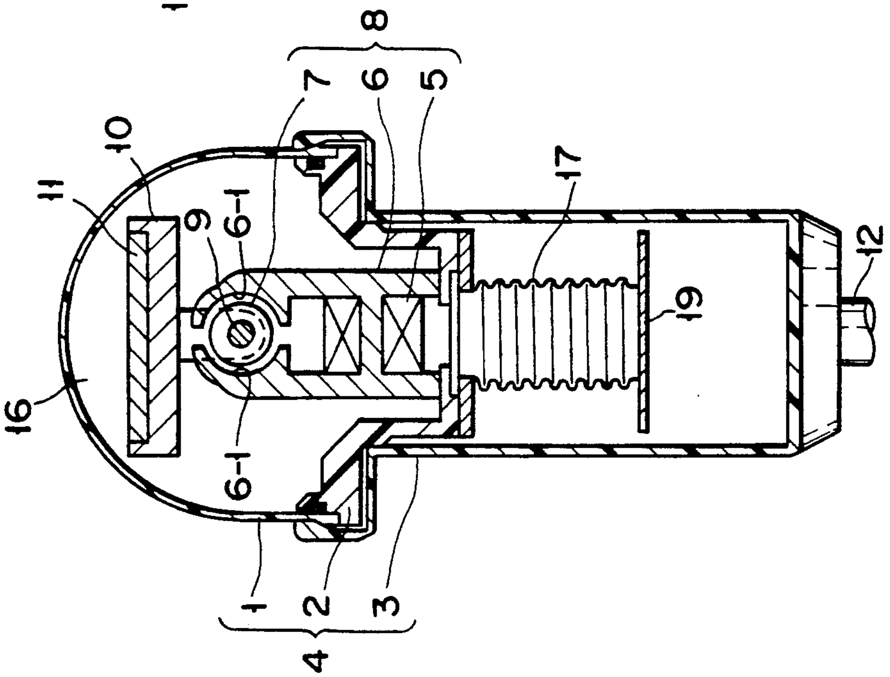
FIG. 7 is a front sectional view of the ultrasonic scanner according to a modification of the first embodiment.

FIG. 6 shows a generated torque relative to the rotational angle of the permanent magnet. It is seen from FIG. 6 that when a swinging range is properly selected from a range of 0° to 180°, torques in the same direction are generated in this swinging range.

Figure 1:
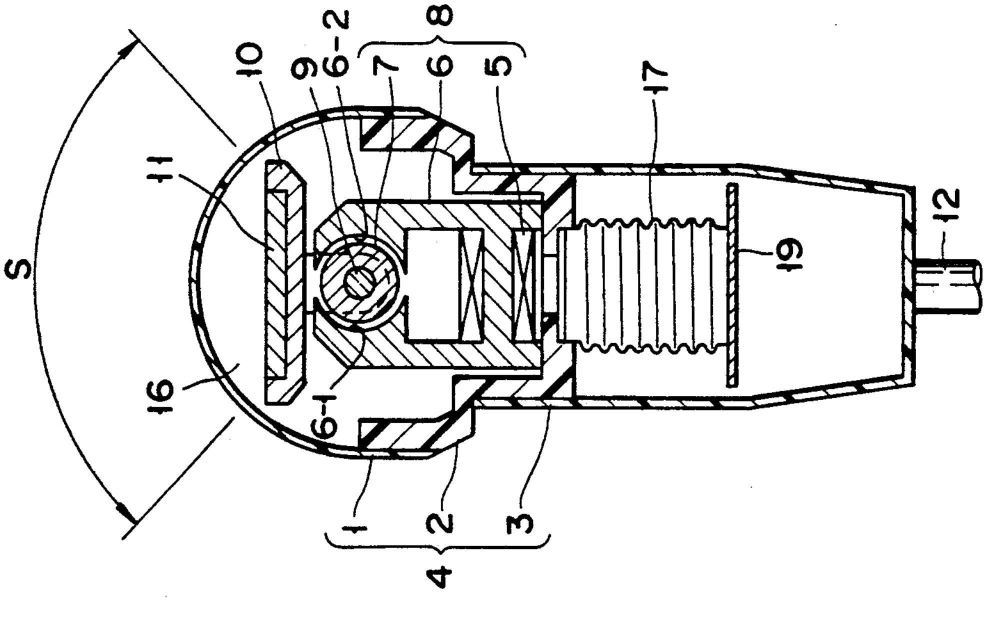
FIG. 1 is a front sectional view of an ultrasonic scanner according to the first embodiment of the present invention.

When the rotating shaft 9 is swung by the swinging motor 8, the transducer element 11 is swung within a sector-shaped range represented by reference symbol S in FIG. 1. Therefore, a living body is scanned by an ultrasonic beam radiated from the transducer element 11 in a sector shape. When a timing to reverse a direction of the current supplied to the exciting coil 5 is changed, the scanning region S can be arbitrarily set, as a matter of course. Note that power required to drive the motor, power required to generate an ultrasonic beam from the transducer element, and a control signal for the motor and the transducer element are supplied through a cable 12.

In the first embodiment, there is provided a magnetic sensor 15 for detecting a swinging angle of the transducer element 11. The sensor 15 includes a permanent magnet (first or second member) 13 fixed to the distal end of the extending member 10-1 of the support member 10, and a pair of magnetoresistive elements (first or second members) 14-1 and 14-2 each of which has an arcuated shape to be opposite to a swinging locus of the permanent magnet 13, is fixed to the shielding case 2, and changes a resistance in correspondence with a change in strength of a magnetic field (see FIGS. 2 and 3).

A magnetic field generated by the permanent magnet 13 is applied to the magnetoresistive elements 14-1 and 14-2. In this state, if the permanent magnet 13 is swung in the clockwise direction in FIG. 3, the strength of the magnetic field applied to the magnetoresistive element 14-1 is increased. On the other hand, the strength of the magnetic field applied to the magnetoresistive element 14-2 is decreased. Therefore, a resistance of the magnetoresistive element 14-1 is largely changed. On the other hand, a resistance of the magnetoresistive element 14-2 is slightly changed. When a difference between these resistances is detected, a swinging angle of the permanent magnet 13, i.e., a swinging angle of the transducer element 11, is detected.

Even if the housing 4 contains a sound transmitting medium, therefore, a magnetic field generated by the detecting means is not adversely affected by the sound transmitting medium. Therefore, a swinging angle of the transducer element can be accurately detected, and hence a radiating/returning direction of an ultrasonic beam can be accurately detected, thus accurately reconstructing an image.

In addition, since the swinging angle of the transducer element is accurately detected, the position of the transducer element can be controlled with high precision. When the precision of control is low, the support member 10 may often collide with the stator 6. In the first embodiment, however, there is no possibility of such a collision, and a long service life of the ultrasonic scanner can be achieved.

Furthermore, when a swinging angle of the transducer element is magnetically detected, power consumption of the sensor is small as compared with a case wherein the swinging angle is optically detected. Therefore, power cost can be saved in the first embodiment.

FIGS. 7 to 10 show a modification of the first embodiment. In this modification, as is most apparent from FIGS. 8 and 9, the permanent magnet 13 is mounted at one end of the rotating shaft 9, and the pair of semicircular magnetoresistive elements 14-1 and 14-2 are mounted to the shielding case to be opposite to the permanent magnet 13. An operation of the sensor including the permanent magnet 13 and the magnetoresistive elements 14-1 and 14-2 is the same as that in the first embodiment. In this case, a swinging locus of the permanent magnet 13 is decreased, and the size of each magnetoresistive element 14-1 or 14-2 is also decreased. Therefore, a space for the sensor 15 can be saved. In addition, since the swinging locus of the permanent magnet 13 is decreased, bubbles are not easily formed in the sound transmitting medium (a reason for this merit will be described hereinafter).

In addition, the permanent magnet may be mounted on the shield case 2 and the magnetoresistive elements may be mounted on the extending member 10-1 or the rotating shaft 9.

As shown in FIGS. 1 to 4, the ultrasonic scanner according to the first embodiment includes a means for compressing the sound transmitting medium filled in the chamber 16.

More specifically, a bellows 17 is mounted at a bottom portion of the shielding case 2. The internal space of the bellows 17 is filled with a sound transmitting medium. This internal space defines a supplement medium container. This internal space communicates with the inside of the chamber 16 through two holes 21 formed in the bottom portion of the shielding case 2. In addition, a plurality of support shafts 18 are fixed to the bottom portion of the shielding case 2. A lower end of each support shaft 18 is formed into a male screw. The lower end of each male screw extends through a support plate 19 mounted at the bottom portion of the bellows 17, and is threadably engaged with a corresponding nut 20.

When the nut 20 is fastened to the male screw at the lower end of each support shaft 18 after the sound transmitting medium is filled in the chamber 16 and the internal space of the bellows 17, an internal capacity of the bellows 17 is decreased. Therefore, the sound transmitting medium in the chamber 16 is compressed.

Conventionally, when the transducer element is swung in the sound transmitting medium at high speed, heat is generated by swinging. As a result, bubbles may often be formed in the sound transmitting medium Since the bubbles interrupt transmission of ultrasonic beams, a high-quality image cannot be obtained. Conventionally, therefore, an operation to eliminate bubbles is frequently performed. However, it is difficult to perfectly eliminate bubbles.

In contrast to this, in the first embodiment, the bellows 17 always compresses the sound transmitting medium filled in the space surrounded by the cap 1 and the shielding case 2 by an urging pressure thereof. Therefore, a liquid pressure of the sound transmitting medium is increased to increase an air saturation pressure of the transmitting medium. For this reason, formation of bubbles is suppressed. Therefore, an image having a quality higher than that of the conventional image can be obtained without interruption for transmission of an ultrasonic beam.

In addition, when the nut 20 is adjusted with respect to the male screw at the lower end of the support shaft 18, the internal capacity of the bellows 17 is changed. Therefore, a compression pressure can be controlled. For example, when the compression pressure is decreased by a change in bellows 17 with the passage of time, the nut 20 is adjusted to set the compression pressure to be a predetermined pressure.

Even if an amount of the sound transmitting medium in the chamber 16 is decreased by formation of bubbles, the bellows is filled with a supplement medium, and hence a new medium is not required. In addition, since an amount of the sound transmitting medium is increased in accordance with the capacity of the bellows 17, a cooling effect for the exciting coil 5 can be enhanced.

FIGS. 7 to 10 show a modification of the first embodiment. The means for changing the internal capacity of the bellows in this modification is slightly different from that in the first embodiment. More specifically, the support shaft 18 has a cylindrical shape, and a female screw is formed inside the cylinder. This female screw is threadably engaged with a male screw shaft 22 fixed to the bottom portion of the shielding case 2. The lower end of the cylindrical support shaft 18 is fitted on and fixed to a pin 23 which extends through a hole formed in the support plate 19. At this time, the lower end of the cylindrical support shaft 18 and the pin 23 are not fixed to the support plate 19.

Figure 8:
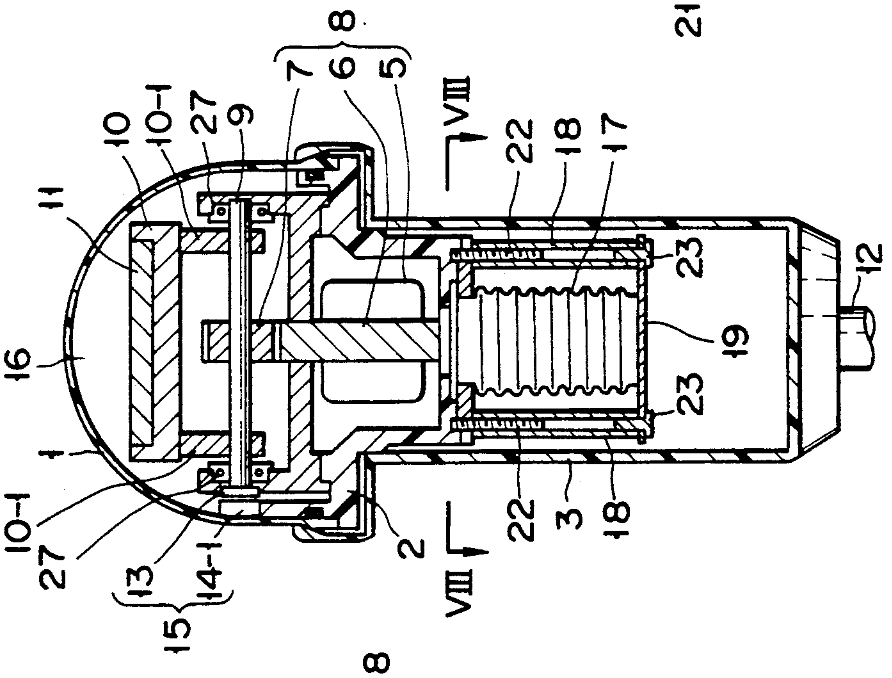
FIG. 8 is a side sectional view of the ultrasonic scanner shown in FIG. 7.
Figure 9:
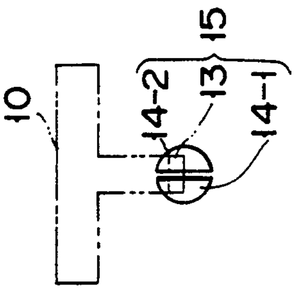
FIG. 9 is a front view of the sensor for detecting a swinging angle of the transducer element arranged in the ultrasonic scanner shown in FIGS. 7 and 8.
Figure 10:
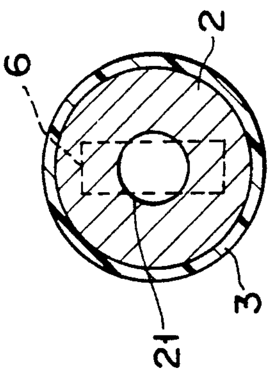
FIG. 10 is a sectional view taken along the line of VIII—VIII of FIG. 8.

When the cylindrical support shaft 18 is rotated, therefore, the position of the support plate 19 is moved to change the internal capacity of the bellows 17. Note that FIG. 8 shows a state in which the support shaft 18 is perfectly in contact with the bottom portion of the shielding case 2, i.e., a state wherein the internal capacity of the bellows is minimum. Therefore, the internal capacity of the bellows can be freely changed within the range of the length which extends from the shielding case 2 of the total length of the male screw shaft 22. Note that the lower end of the support shaft 18 may be inserted in the hole formed in the support plate 19 without being fixed.

Figure 11:
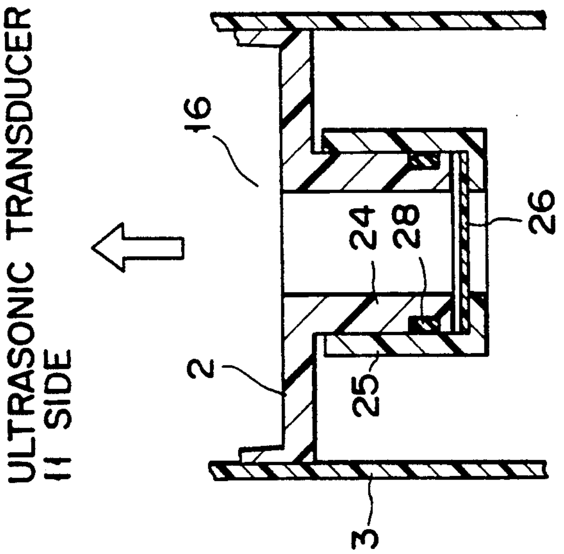

FIG. 11 shows the second modification of the compressing means. In this modification, a first sleeve 24 having an outer surface on which a male screw is formed is arranged at the bottom portion of the shielding case 2. A second sleeve 25 having an inner surface on which a female screw is formed is threadably engaged with the first sleeve 24. An elastic plate 26 consisting of, e.g., a rubber is disposed at a lower portion of the second sleeve 25 An O-ring 28 seals between the first and second sleeves 24 and 25.

When the second sleeve 25 is moved with respect to the first sleeve 24 after the chamber 16 and the internal space of the first and second sleeves 24 and 25 are filled with a sound transmitting medium, therefore, the capacities of the internal spaces of the first and second sleeves are decreased. At this time, the elastic plate 26 is expanded in a direction opposite to the moving direction of the second sleeve 25. However, since a restoring force of the elastic plate 26 is affected by the sound transmitting medium in the chamber 16, the sound transmitting medium in the chamber 16 is compressed.

Thus, the restoring force of the elastic plate 26 always compresses the sound transmitting medium filled in the chamber 16. Therefore, formation of bubbles is suppressed. In addition, when the second sleeve 25 is moved with respect to the first sleeve 24, the capacities of the internal spaces of the first and second sleeves 24 and 25 are changed, and hence the compression pressure can be controlled.

Figure 12:
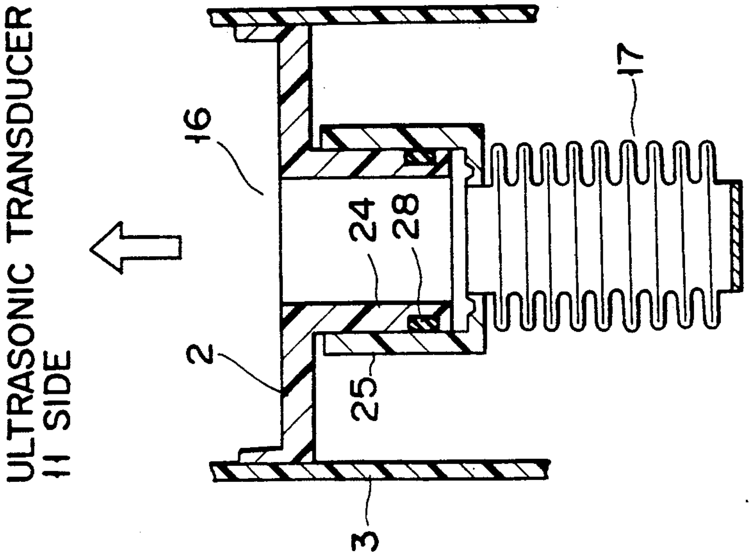
FIGS. 11 to 13 are sectional views showing modifications of a means for compressing a sound transmitting medium filled in the ultrasonic scanner

As shown in FIG. 12, the bellows 17 can be used in place of the elastic plate 26. An operation in this case is the same as that in FIG. 9.

Figure 13:
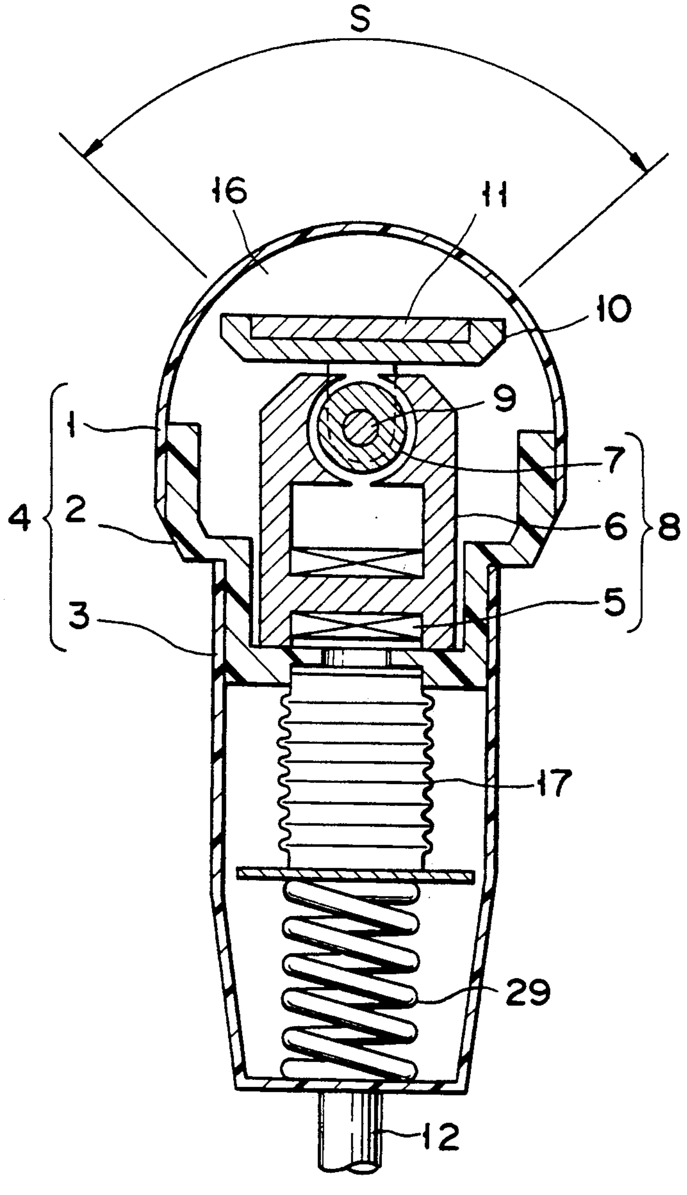

FIG. 13 shows the fourth modification of the compressing means. In this modification, a spring 29 is inserted between the bellows 17 and the holding case 3. In this case, the sound transmitting medium in the chamber 16 is compressed by a biasing force of the spring 29 in addition to the urging pressure of the bellows 17. Therefore, even if the urging pressure of the bellows 17 is degraded over time, a predetermined compression pressure can always be assured.

FIGS. 14 to 18C show an ultrasonic scanner according to the second embodiment of the present invention. In the second embodiment, a transducer element is not directly swung by a swinging motor, but a drive force of swinging movement generated by the swinging motor is transmitted by a parallel link mechanism 40 to the transducer element, thereby swinging it.

Figure 15:
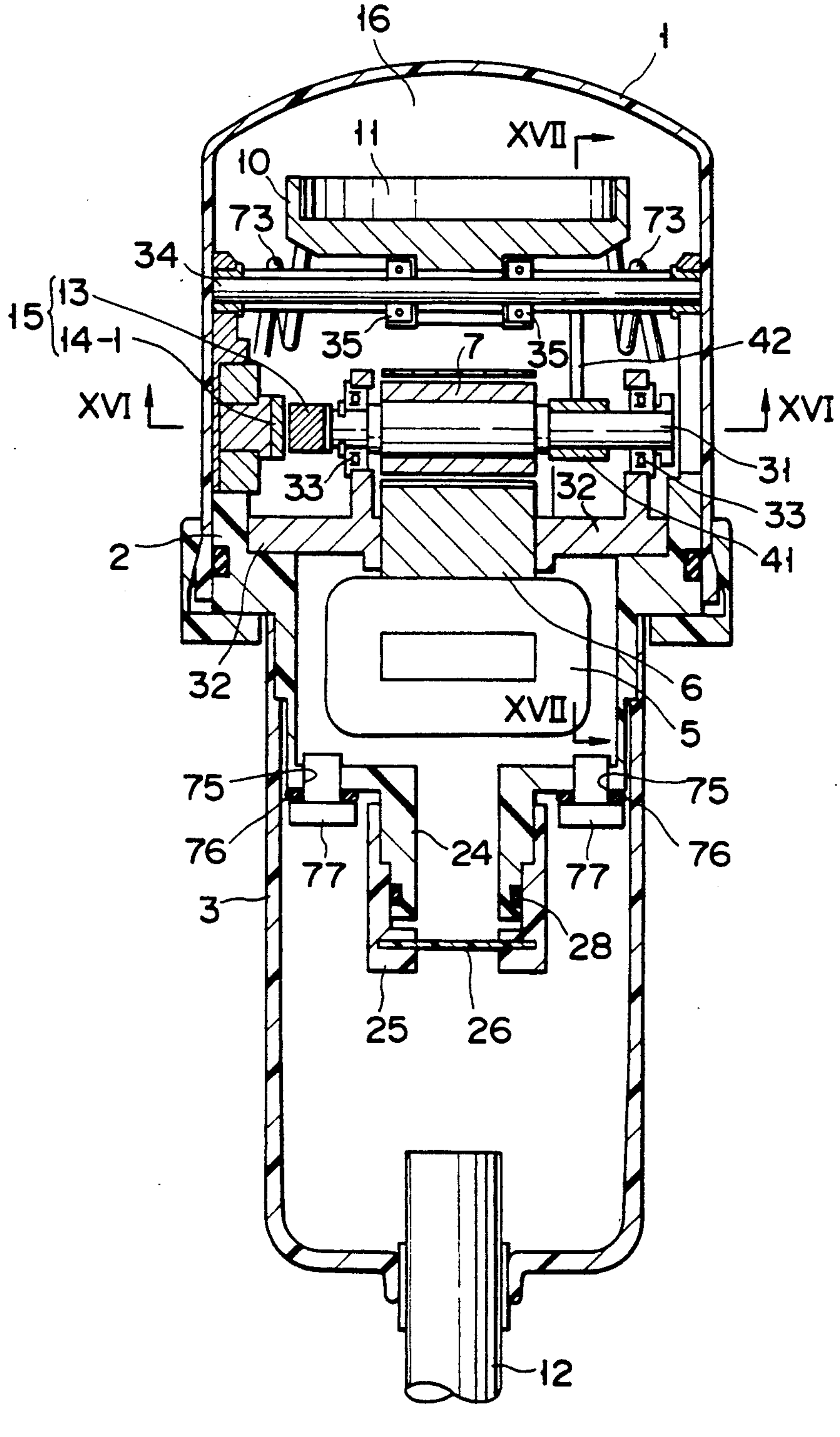
FIG. 15 is a side sectional view of the ultrasonic scanner shown in FIG. 14.

In this embodiment, a swinging motor 8 includes an exciting coil 5, a stator 6, and a rotor 7, as in the first embodiment. A drive shaft 31 fixed to the center of the rotor 7 is rotatably supported by a pair of bearings 33 (FIG. 15) fixed to a braket 32 (FIG. 15). Note that the rotor 7 and the drive shaft 31 may be integrally formed.

On the other hand, a transducer element 11 is supported by a support member 10. The support member 10 is rotatably supported by a stationary shaft 34 (or support shaft), fixed to a shielding case 2, using a pair of bearings 35. The stationary shaft 34 is disposed to be parallel to the drive shaft 31.

Figure 14:
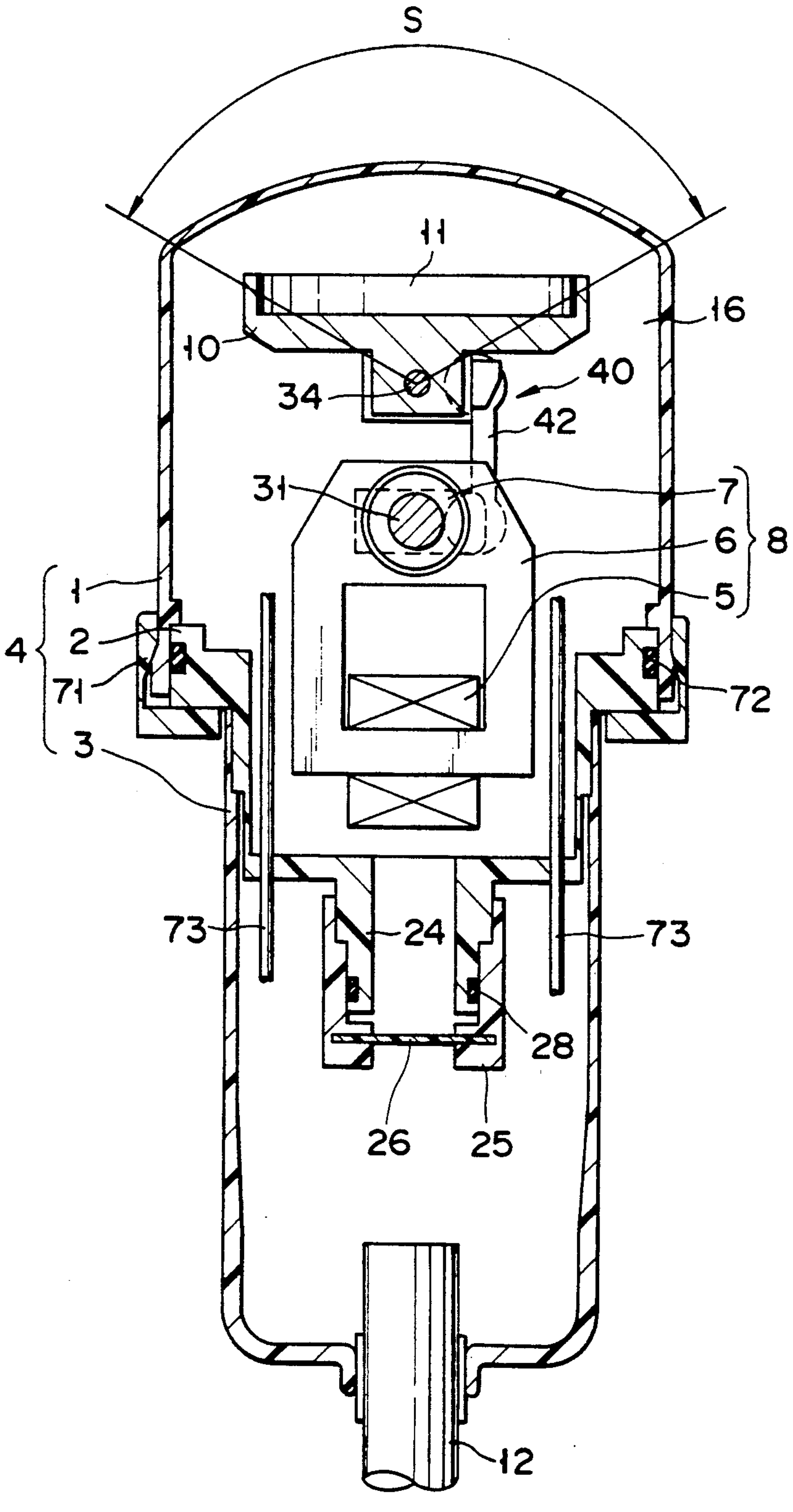
FIG. 14 is a front sectional view of an ultrasonic scanner according to the second embodiment of the present invention.
Figure 16:
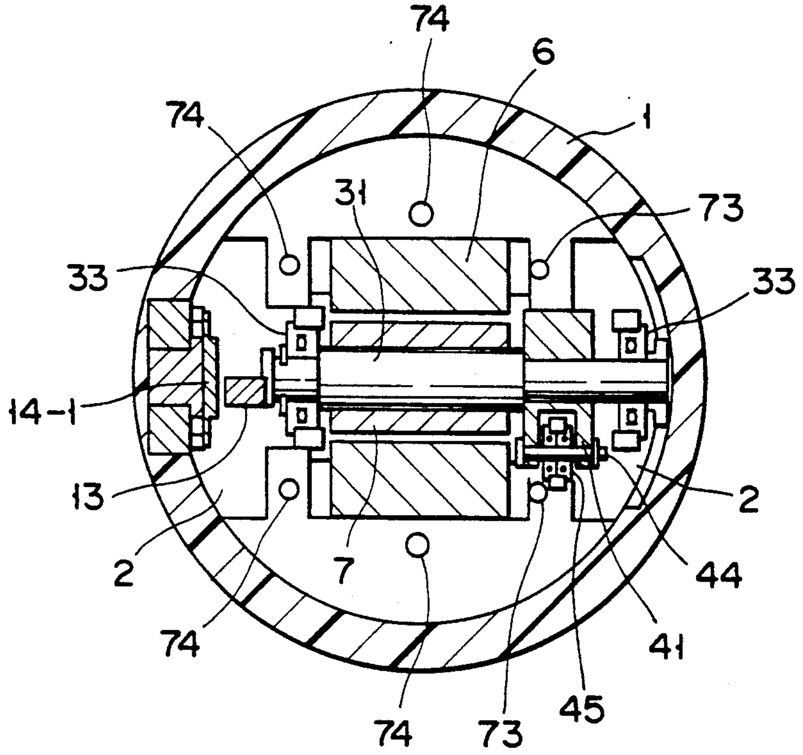
FIG. 16 is a sectional view taken along the line of XVI—XVI of FIG. 15.

In FIG. 14, reference numeral 71 denotes a ring to mount the cap 1 to the shielding case 2. An O-ring 72 seals between the cap 1 and the shielding case 2. Referring to FIGS. 14 and 16, a signal transmission cable 73 supplies an ultrasonic signal to the transducer element 11. An electric cable 74 supplies a current to the exciting coil 5. In addition, in FIG. 15, a supply port 75 is formed in the shielding case 2 to fill a sound transmitting medium in a chamber 16. An O-ring 76 and a plug 77 are mounted at the supply port 75.

Figure 17B:
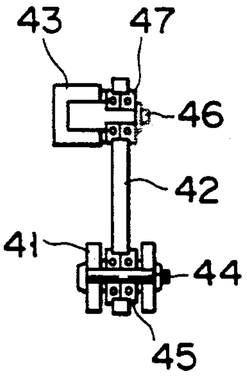
FIG. 17B is a sectional view of a second link member shown in FIG. 17A.
Figure 17A:
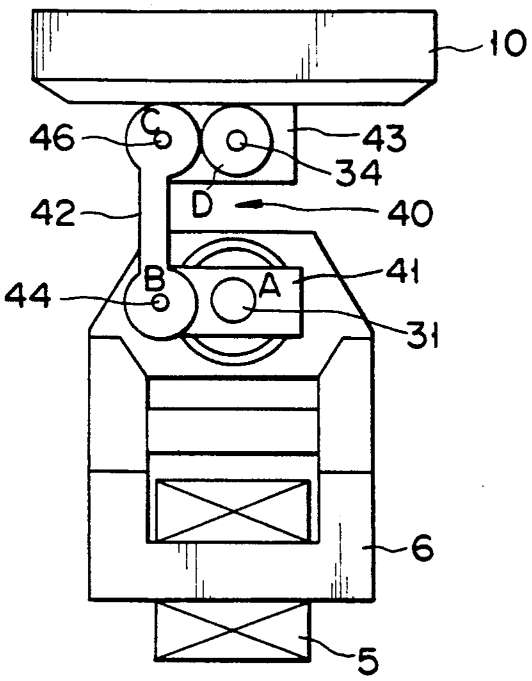
FIG. 17A is a sectional view taken along the line of XVII—XVII of FIG. 15.

As is most apparent from FIGS. 17A and 17B, the parallel link mechanism 40 includes a first link member 41 having a proximal end fixed to the drive shaft 31, a second link member 42 having a proximal end rotatably coupled to the distal end of the first link member 41, and a third link member 43 having a proximal end rotatably coupled to the distal end of the second link member 42 and a distal end rotatably coupled to the stationary shaft 34. Therefore, when the drive shaft 31 is swung, the link members 41 to 43 are moved. As a result, the support member 10 is swung. Note that the shielding case 1 to which the drive shaft 31 and the stationary shaft 34 are mounted defines a stationary link.

More specifically, a pin 44 is mounted at the distal end of the first link member 41. The pin 44 is rotatably supported by a pair of bearings 45 mounted at the proximal end of the second link member 42. On the other hand, the third link member 43 is fixed to the support member 10, and a pin 46 is mounted at the proximal end of the third link member 43. The pin 46 is rotatably supported by a pair of bearings 47 mounted at the distal end of the second link member 42. Note that the second link member 42 is shifted from the first and third link members 41 and 43 in a direction which is perpendicular to the surface of the sheet of FIG. 17A. Therefore, interference of the second link member 42 with respect to the first and third link members 41 and 43 is prevented. In addition, two ends of the second link member 42 are formed to be substantially circular to prevent interference of the second link member 42 with respect to the support member 10 and the stator 6.

Assuming that the central axes of the drive shaft 31, the pins 44 and 46, and the stationary shaft 34 are A, B, C, and D, respectively, $\overline{AB}=\overline{CD}$, and $\overline{BC}=\overline{DA}$. When the parallel link mechanism 40 is driven, a quadrilateral ABCD always constitutes a parallelogram.

Figure 18C:
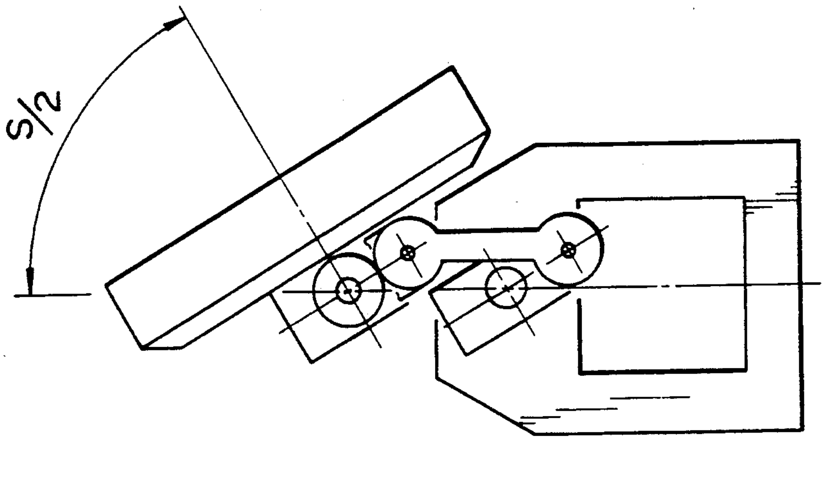
FIGS. 18A to 18C are schematic views for explaining an operation of the ultrasonic scanner shown in FIGS. 14 to 17B.
Figure 18A:
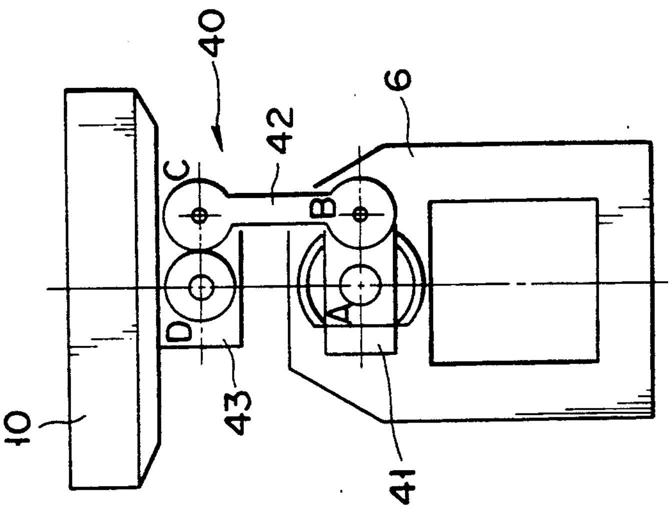
Figure 18B:
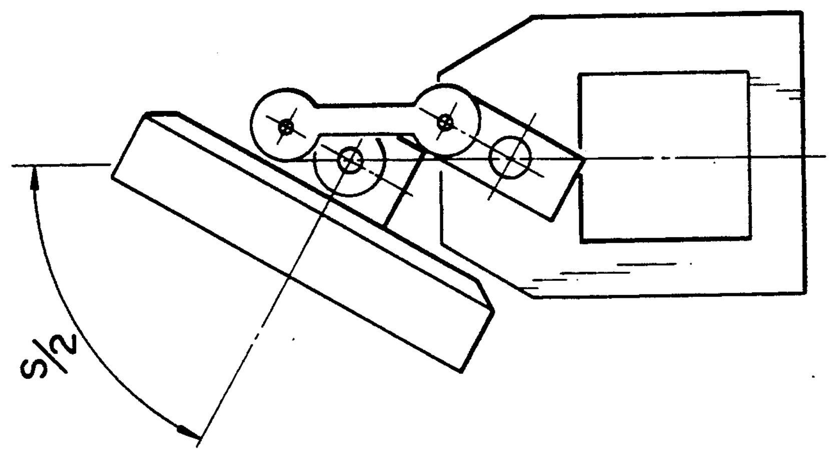

An operation of the second embodiment will be described hereinafter. The swinging motor 8 is swung in the same manner as in the first embodiment. More specifically, the drive shaft 31 is continuously swung. Therefore, a drive force of swinging movement is transmitted to the support member 10 by the parallel link mechanism 40. More specifically, as shown in FIGS. 18A to 18C, the first link member 41 is continuously swung, and the second link member 42 is continuously and vertically moved. Therefore, the third link member 43 and the support member 10 are continuously swung. As a result, the transducer element 11 is swung about the stationary shaft 34 within a sector-shaped range S shown in FIG. 14. As shown in FIGS. 18A and 18C, the transducer element and the support member 10 are swung through an angle of S/2 with respect to the central line. For example, therefore, the transducer element can be swung clockwise through an angle of only S/2 from the central line. On the contrary, the transducer element can be swung counterclockwise through an angle of only S/2 from the central line. In addition, the swinging range S can be freely changed.

Furthermore, the drive shaft 31 and the stationary shaft 34 are coupled to each other by the parallel link mechanism, and $\overline{AB} \parallel \overline{CD}$ and $\overline{BC} \parallel \overline{DA}$ even if the drive shaft 31 has any swinging angle. Therefore, $\overline{AB}$ and $\overline{CD}$ are always swung at the same angular velocity, and hence the swinging angle of the support member 10 is always equal to that of the drive shaft 31. For this reason, in this embodiment, the swinging angle of the support member 10 is not directly detected by a sensor, but the swinging angle of the drive shaft 31 is detected by the sensor, thus obtaining the swinging angle of the support member 10.

Conventionally, a cable or a pulley is used as a means for transmitting a drive force of swinging movement from the swinging motor to the transducer element. In this case, bending stress is generated in the cable. The smaller the diameter of the pulley is, the larger the bending stress. Therefore, it is difficult to decrease the diameter of the pulley in consideration of a service life of the cable. As a result, it is difficult to decrease the size of the ultrasonic scanner. A gear is often used as a transmitting means in place of the cable or pulley. In this case, the gear teeth must be formed with high manufacturing precision, and it is difficult to decrease the size of the ultrasonic scanner. In addition, the gear teeth are worn and degraded with the passage of time. As a result, backlash of the gear teeth occurs to shorten the service life of the ultrasonic scanner.

In contrast to this, the parallel link mechanism 40 is used as a transmitting means in the second embodiment. Therefore, bending stress of the cable is negligible, unlike in a case wherein a cable or pulley is used as a transmitting means, thus achieving a small-sized ultrasonic scanner. In addition, high precision of the manufacture of the transmitting means is not required, unlike in the case wherein a gear is used as a transmitting means. Therefore, a change with the passage of time such as backlash does not occur to achieve a long service life of the scanner.

In addition, the swinging center (i.e., the stationary shaft 34) of the support member 10 can be arbitrarily set. For this reason, a swinging radius of the support member 10 can be sufficiently decreased. Therefore, a load inertia obtained when the support member 10 is swung can be easily reduced to minimize generation of vibrations. Furthermore, since a swinging radius of the support member is decreased, the diameter of the scanner is necessarily decreased to easily achieve a compact scanner, and to improve its operability. In addition, since a swinging radium of the support member is decreased, a swinging range of the transducer element can be wider than that of the conventional scanner even if the swinging range of the support member is equal to that of the conventional scanner Therefore, an ultrasonic beam radiating range of the transducer element is increased, and an amount of data of a living body image can be largely increased. For this reason, in particular, this scanner is advantageous in a B-mode operation.

Note that although the parallel link mechanism is arranged on only one side of the rotor 7 in this embodiment, the parallel link mechanisms may be arranged on both sides of the rotor 7.

Figure 19C:
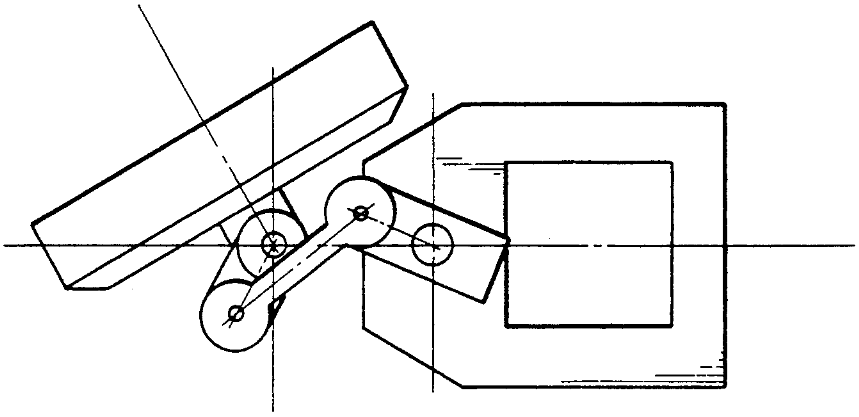
FIGS. 19A to 19C are schematic views for explaining an operation of the ultrasonic scanner according to the first modification of the second embodiment
Figure 19A:
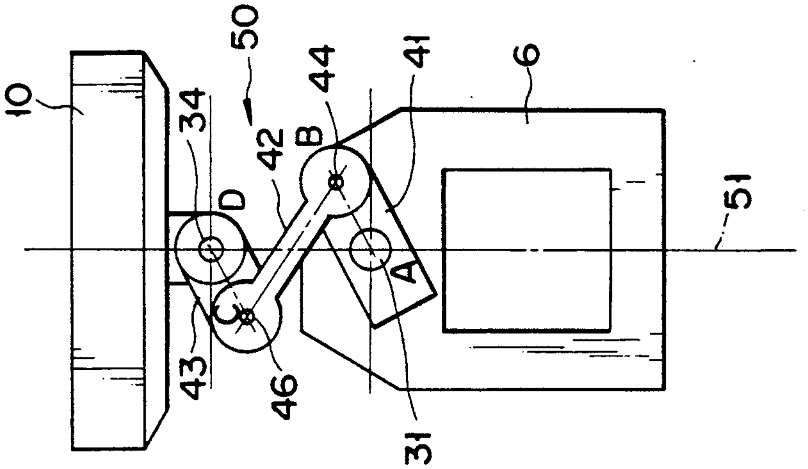
Figure 19B:
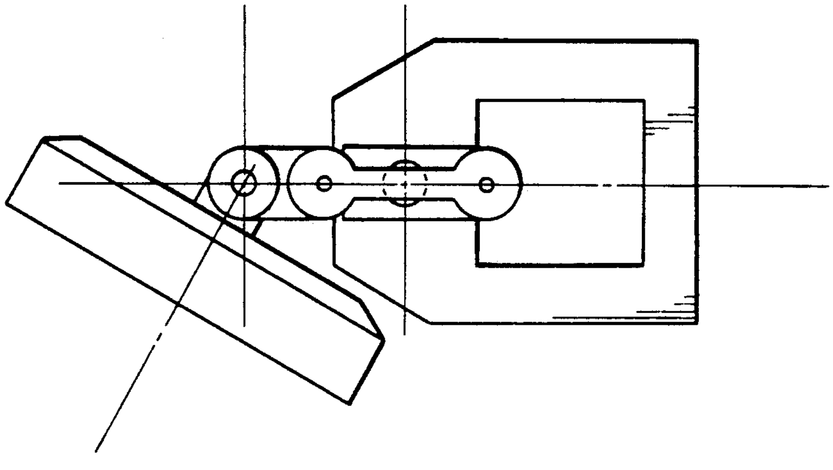
Figure 20:
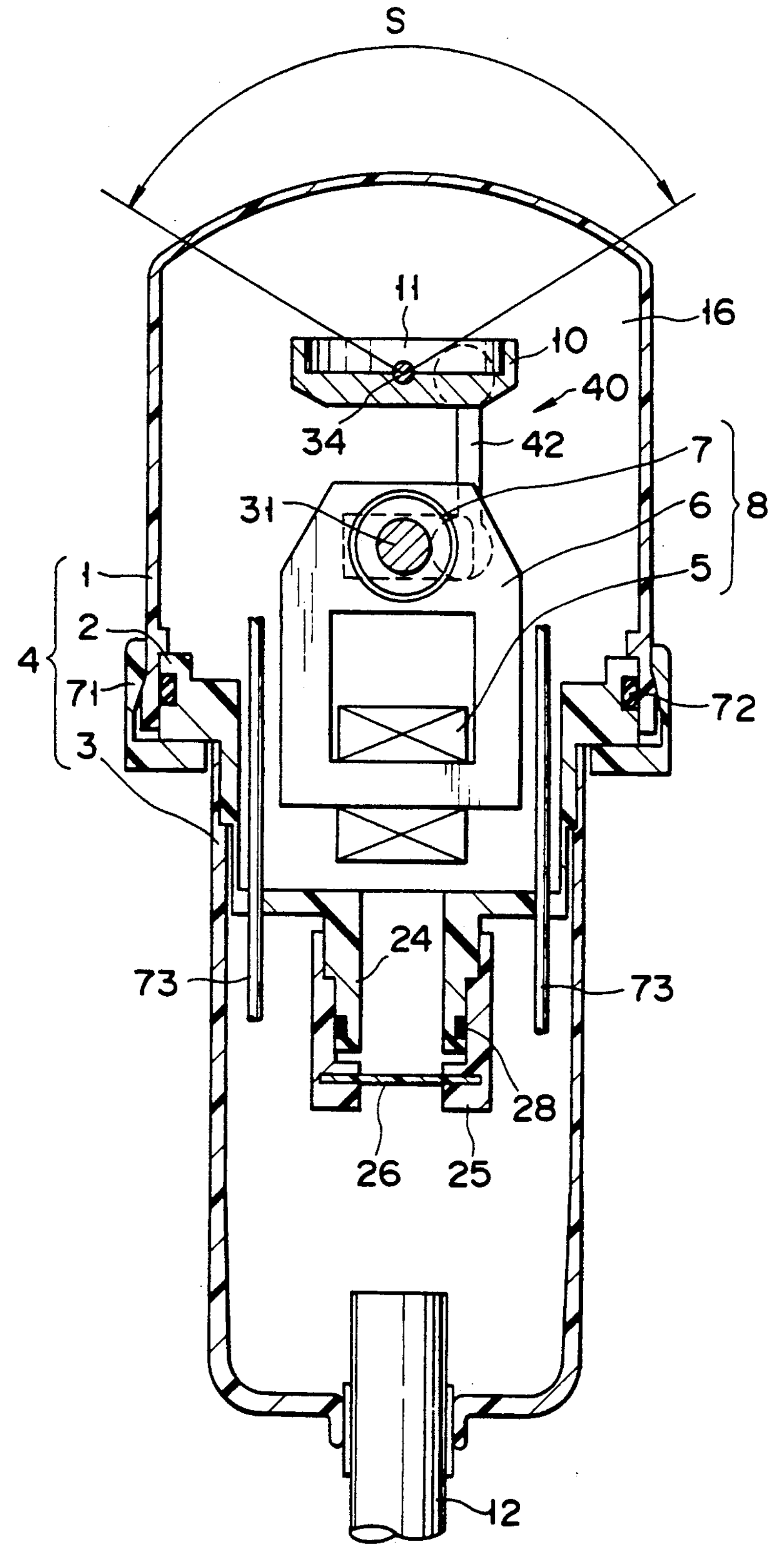
FIG. 20 is a front sectional view of the ultrasonic scanner according to the second modification of the second embodiment.
Figure 21:
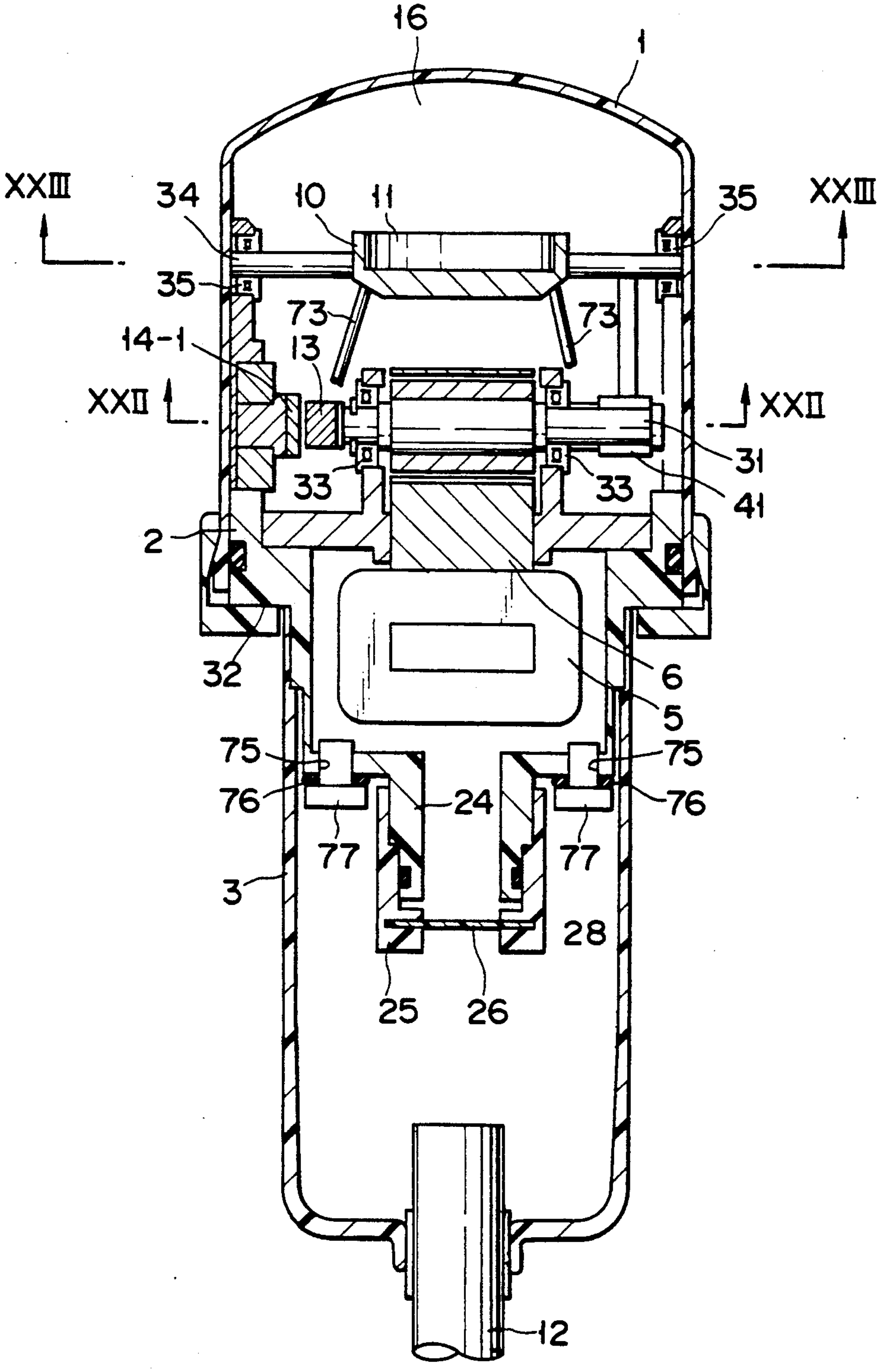
FIG. 21 is a side sectional view of the ultrasonic scanner shown in FIG. 20.
Figure 22:
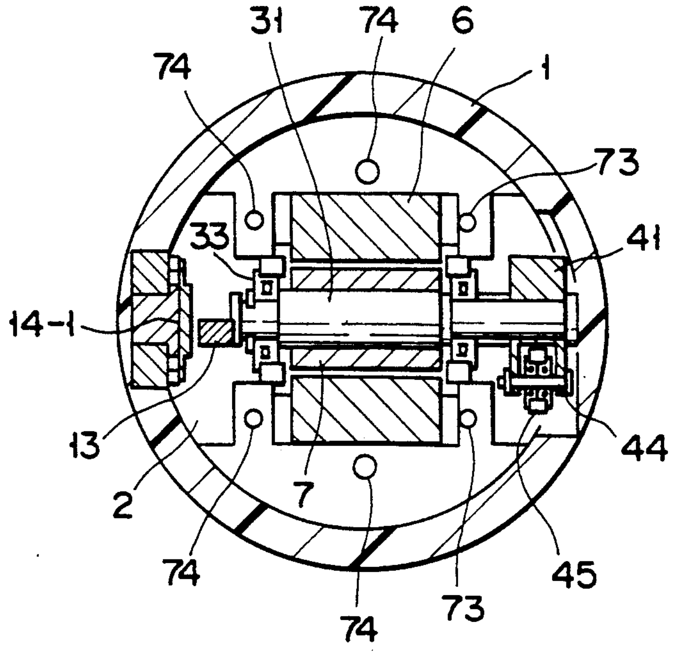
FIG. 22 is a sectional view taken along the line of XXII—of FIG. 21.
Figure 23:
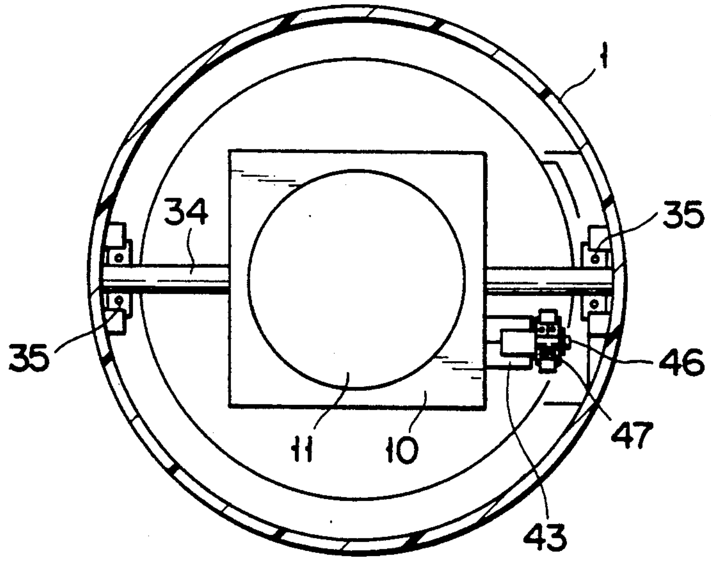
FIG. 23 is a sectional view taken along the line of XXIII—XXIII of FIG. 21.

FIGS. 19A to 19C show the first modification of the second embodiment. In this modification, an anti-parallel link mechanism 50 is used in place of the parallel link mechanism. More specifically, the pins 44 and 46 are positioned on the opposite sides with respect to a central line 51. Assuming that the central axes of the drive shaft 31, the pins 44 and 46, and the stationary shaft 34 are A, B, C, and D, respectively, a line which connects the point B to the point C intersects with a line which connects the point A to the point D, and $\overline{AB}=\overline{CD}$, and $\overline{BC}=\overline{DA}$. For this reason, in this case, when the drive shaft 31 is continuously swung, the first link member 41 is continuously swung, and the second link member 42 is continuously and vertically moved and swung. Therefore, as shown in FIGS. 19A and 19C, the third link member 43 and the support member 10 are continuously swung. Therefore, this modification can exhibit the same effect as in the second embodiment.

In this modification, however, the first and third link members 41 and 43 are swung in opposite directions at different angular velocities. At this time, a speed ratio $i=\overline{DA}/\overline{AE}$, where E is the intersecting point between the axis of the second link member 42 and the central line 51. Therefore, in order to swing the transducer element at a constant speed, the swinging speed of the drive shaft 31 must be controlled in consideration of the speed ratio i.

Therefore, the transmitting means is not limited to the parallel link mechanism, and various link mechanisms can be applied to the second embodiment.

FIGS. 20 to 23 show the second modification of the second embodiment. In this modification, the swinging center (i.e., a central axis of the rotatory shaft or support shaft 34) of the support member 10 coincides with the swinging center of an ultrasonic beam radiated from the transducer element 11. As is most apparent from FIGS. 20 and 23, the rotatory shaft 34 extends from a portion of the support member 10 corresponding to the center of the transducer element 11. The second link member 42 is shifted in the extending direction of the rotatory shaft 34 to prevent interference between the support member 10 and the second link member 42 of the parallel link mechanism 40.

In this modification, therefore, the swinging center of the support member 10 coincides with the swinging center of an ultrasonic beam radiated from the transducer element 11, and hence a swinging radius of the support member 10 can be sufficiently decreased. Therefore, a load inertia obtained when the support member 10 is swung is reduced to minimize generation of vibrations. In addition, since the swinging radius of the support member is decreased, the diameter of the scanner is necessarily decreased, thus easily achieving a compact scanner. Furthermore, since the swinging radius of the support member is decreased, the swinging range of the transducer element can be wider than that in the second embodiment even if the swinging range of the support member is equal to that in the second embodiment. As a result, an ultrasonic beam radiating range of the transducer element can be increased to further increase an amount of data of an image. Therefore, a conventional drawback that radiation of an ultrasonic beam is interrupted by ribs when, e.g., a heart is diagnosed can be solved.

Figure 24C:
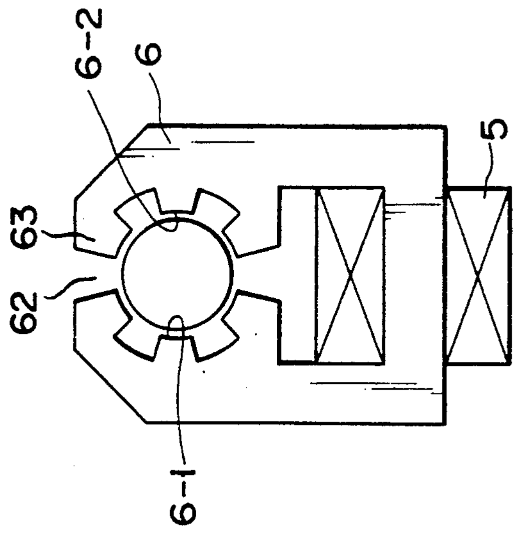
FIGS. 24A to 24C are schematic views showing a swinging motor arranged in the ultrasonic scanner according to the present invention.
Figure 24B:
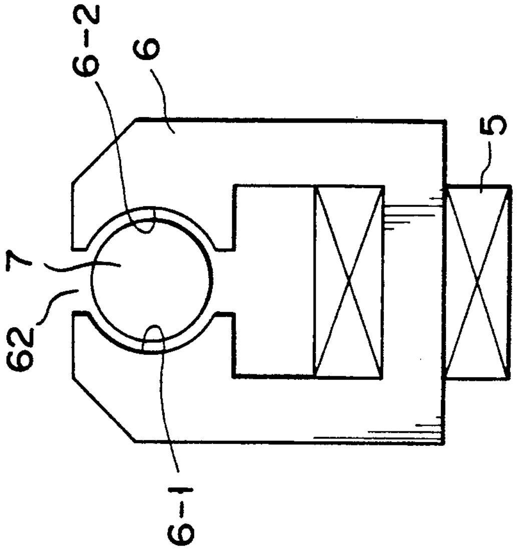
Figure 24A:
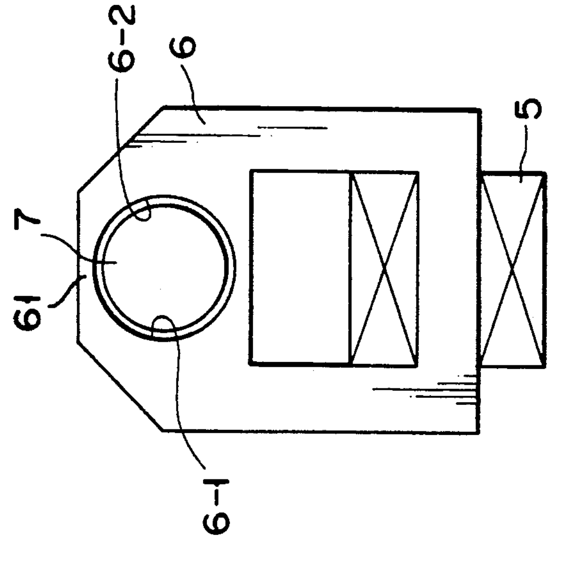

FIGS. 24A to 24C show various arrangements of the stator of the swinging motor. In the stator shown in FIG. 24A, a pair of opposite surfaces 6-1 and 6-2 which respectively define magnetic poles are coupled to each other by a thin-wall portion 61 (closed slot shape). In the stator shown in FIG. 24B, a gap 62 is formed between the pair of opposite surfaces 6-1 and 6-2 (open slot shape). In the stator shown in FIG. 24C, the gap 62 is formed between the pair of opposite surfaces 6-1 and 6-2 (open slot shape), and projecting and recessed portions (internal teeth) 63 are formed on the pair of opposite surfaces 6-1 and 6-2.

These swinging motors have response performance which is better than that of the conventional swinging motor. More specifically, in the conventional swinging motor used in the ultrasonic scanner, a cylinder positioned outside a stationary shaft is swung with respect to the stationary shaft positioned at the center of the motor. Therefore, an inertia moment of the swung cylinder is relatively large. For this reason, when the cylinder is swung, a long time period may often be required until the cylinder is swung at a predetermined speed. In addition, when the cylinder is stopped, the cylinder may not be stopped at a predetermined position, but the cylinder often exceeds the predetermined position. The conventional swinging motor has, therefore, poor response performance.

In contrast to this, in each swinging motor shown in FIGS. 24A to 24C, the rotor 7 having a relatively small inertia moment is swung. Therefore, this swinging motor achieves good response performance of the rotor 7 when the rotor 7 is swung or stopped.

In addition, the magnitude of a cogging torque (a torque obtained when magnetomotive force =0) generated from each swinging motor shown in FIGS. 24A to 24C will be considered hereinafter.

Figure 25:
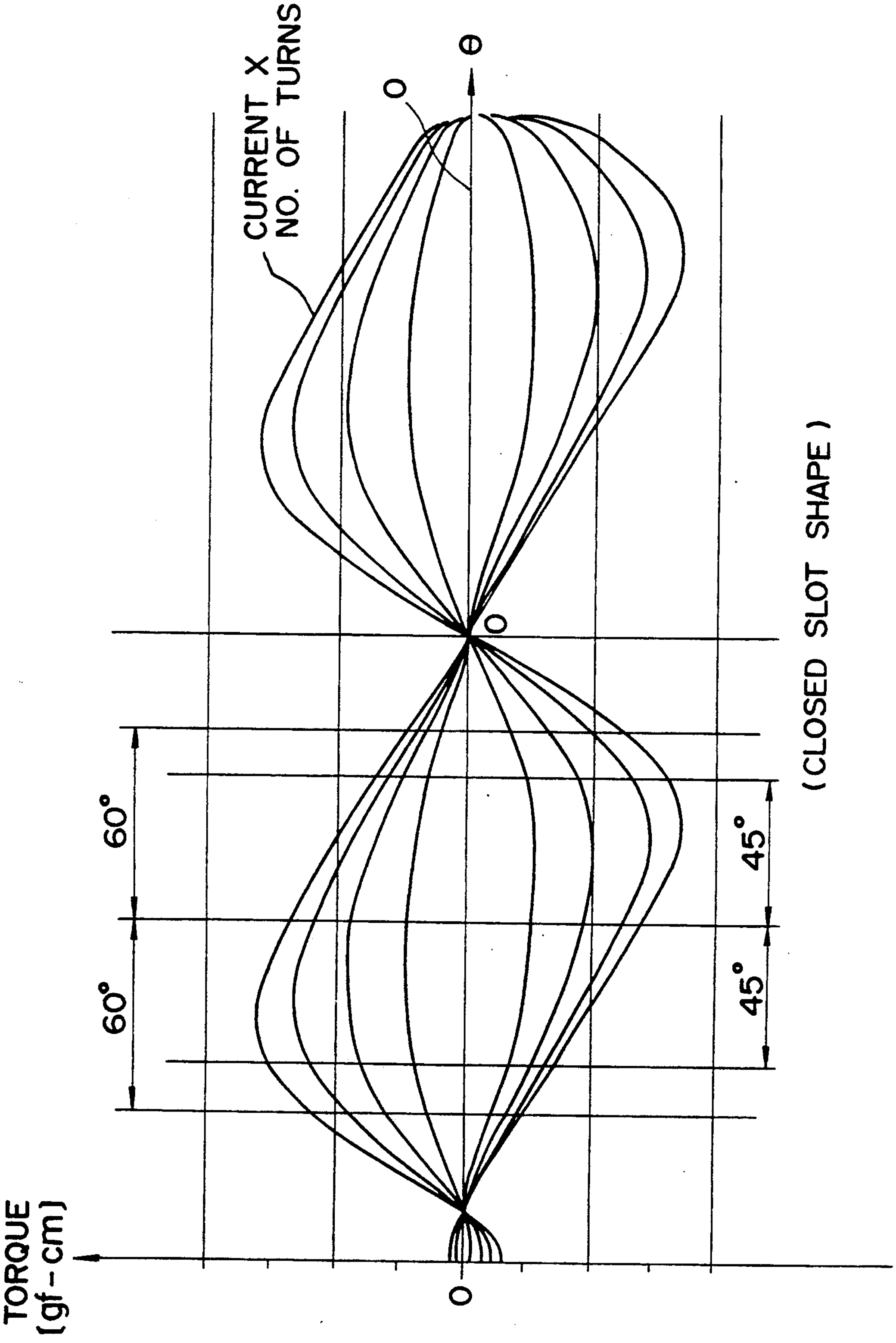
FIGS. 25 to 27 are graphs showing contour lines each representing a product of a current supplied to an exciting coil and the number of turns of the exciting coil (a longitudinal axis of ordinate represents a torque generated in a rotor, and a lateral axis of abscissa represents a rotational angle of the rotor), and are corresponded with the swinging motors shown in FIGS. 24A, 24B, and 24C, respectively.
Figure 26:
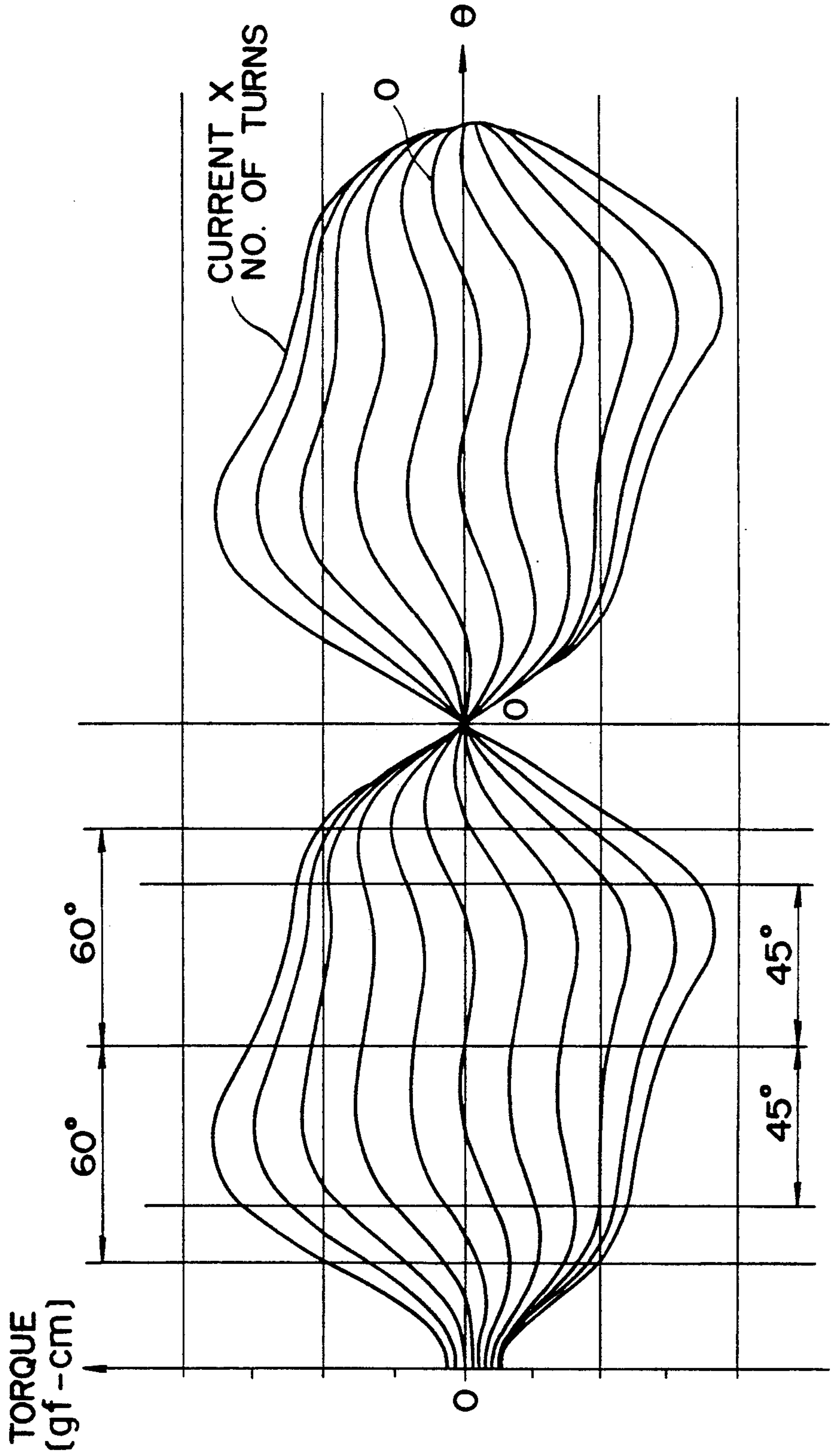
Figure 27:
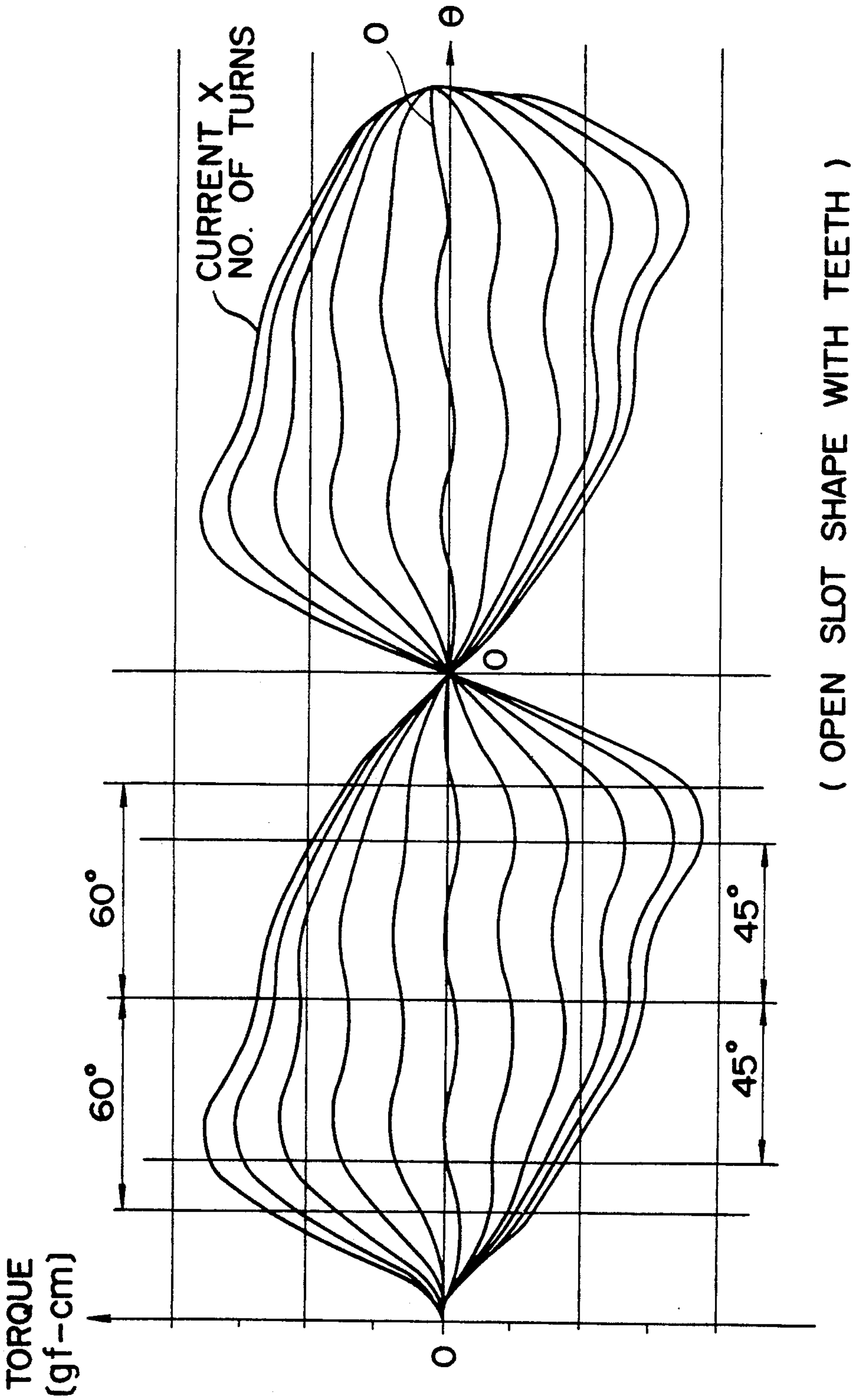

FIGS. 25 to 27 show contour lines representing a product of a current supplied to the exciting coil 5 and the number of turns of the exciting coil 5. The axis of ordinate represents a torque generated in the rotor 7, and the axis of abscissa represents a rotational angle of the rotor 7.

In the stator having a closed slot shape shown in FIG. 25, a curve obtained when a product (magnetomotive force) of a current supplied to the exciting coil 5 and the number of turns of the exciting coil 5 is "0" coincides with an axis wherein a generated torque is "0" at any rotational angle of the rotor 7. This means that an attractive force is not generated between the rotor 7 serving as a permanent magnet and the stator 6, when a current is not supplied to the exciting coil 5. If current supply to the exciting coil 5 is stopped when the transducer element reaches a desired position in M-mode control, the transducer element can always be stopped and held at the desired position.

In contrast to this, in the stator having an open slot shape shown in FIG. 26, a cogging torque is generated. It is, therefore, considered that generation of the cogging torque depends on the presence/absence of the thin-wall portion 61 which couples the pair of opposite surfaces 6-1 and 6-2 to each other. In this stator having the open slot shape, even if current supplying to the exciting coil is stopped when the transducer element reaches the desired position, the transducer element is not stopped at this position, but stops exceeding the position.

In addition, in the stator having an open slot shape with the projecting and recessed portions (internal teeth) 63 shown in FIG. 27, a cogging torque is present. However, the magnitude of the cogging torque is smaller than that in FIG. 26. Furthermore, the number of angles at which the cogging torque is set to be "0" is larger than that in FIG. 26. This is because a cogging torque is dispersed to decrease a peak value as a result of addition of the projecting and recessed portions (internal teeth) 63. Therefore, in order to improve controllability in an M mode in the stator having the open slot shape, the projecting and recessed portions (internal teeth) 63 need only be additionally arranged on the pair of opposite surfaces 6-1 and 6-2, and more preferably, the number of projecting and recessed portions (internal teeth) 63 is increased as much as possible to disperse a cogging torque.

As described above, it is understood that a stator having a closed slot shape is most preferable from a view point of prevention of generation of a cogging torque. Even if the stator has an open sot shape, addition of the projecting and recessed portions (internal teeth) 63 suppresses generation of a cogging torque.

Additional advantages and modifications will readily occur to those skilled in the art. Therefore, the invention in its broader aspects is not limited to the specific details, representative devices, and illustrated examples shown and described. Accordingly, departures may be made from such details without departing from the spirit or scope of the general inventive concept as defined by the appended claims and their equivalents.

What is claimed is:

1. A mechanical ultrasonic scanner for providing an ultrasonic scanning beam comprising:

a housing;

a transducer element arranged in said housing;

means for swinging said transducer element; and means for detecting a swinging angle of said transducer element, said detecting means including a first member which is swung together with said transducer element, and a second member having front and rear surfaces and attached to said housing in a manner such that the rear surface of said second member is in contact with the housing and the front surface of the second member faces to a part of a front surface of said first member which defines a swinging locus plane of the first member, said detecting means causing one of the first and second members to generate a magnetic field at least in a space between the front surface of the second member and the part of the swinging locus plane of the first member, causing the other of the first and second members to detect a strength of the magnetic field which changes in correspondence with a swinging angle of the first member, and detecting the swinging angle of said transducer element on the basis of the change in strength of the detected magnetic field.

2. A scanner according to claim 1, wherein one of the first and second members is a permanent magnet, and the other is a magnetoresistive element.

3. A scanner according to claim 1, wherein the second member is fixed to said housing in correspondence with a part of the swinging locus plane of the first member.

4. A scanner according to claim 1, wherein the second member is formed to have an arcuated shape in correspondence with a part of the swinging locus plane of the first member.

5. A scanner according to claim 1, wherein the second member is semi-circularly formed to be opposite to the first member.

6. A scanner according to claim 1, further comprising:

a liquid sound transmitting medium which is contained in said housing, and in which said transducer element is dipped; and compressing means for compressing said sound transmitting medium in said housing, whereby formation of bubbles from said sound transmitting medium is prevented.

7. A scanner according to claim 6, wherein said swinging means includes drive force generating means having a drive shaft for generating a drive force of swinging movement, and a link mechanism for transmitting the drive force from said drive force generating means to said transducer element, said link mechanism including (a) a first link member having a distal end and a proximal end which is fixed to said drive shaft, (b) a second link member having a distal end and a proximal end which is rotatably coupled to said distal end of said first link member, and (c) a third link member which has a proximal end rotatably coupled to said distal end of said second link member, and a distal end rotatably supported in said housing, said transducer element coupled to the third link member, whereby when said drive shaft is swung, said link members in said link mechanism are moved, so that said transducer element is swung.

8. A scanner according to claim 7, wherein said drive shaft is made of said permanent magnet having one side, in a radial direction, serving as a north pole and the other side, in the radial direction, serving as a south pole, and said drive force generating means includes, a stator having a pair of opposite surfaces arranged to sandwich said drive shaft, and coil means for periodically exciting said pair of opposite surfaces of said stator, so that said pair of opposite surfaces are periodically magnetized to north and south poles to swing said drive shaft.

9. A mechanical ultrasonic scanner, comprising:

a volume-rigid housing;

a transducer element arranged in said housing;

means for swinging said transducer element;

a liquid sound transmitting medium which is contained in said housing, and in which said transducer element is dipped; and means for adjustably compressing said sound transmitting medium in said housing with respect to ambient, at least during the scanning of said transducer, whereby formation of bubbles from said sound transmitting medium is prevented.

10. A scanner according to claim 9, wherein said housing includes a chamber for containing said transducer element and said sound transmitting medium, and said compressing means includes a bellows having an internal space communicating with said chamber and containing sound transmitting medium, the bellows elastically urging said sound transmitting medium in the internal space to compress said sound transmitting medium in said chamber.

11. A scanner according to claim 10, wherein said compressing means includes means for adjusting a capacity of the internal space of said bellows to adjust a compression pressure.

12. A scanner according to claim 9, wherein said housing includes a chamber for containing said transducer element and said sound transmitting medium, and said compressing means includes space defining means for defining an internal space which contains sound transmitting medium and communicates with said chamber, and elastic means for elastically urging said sound transmitting medium in the internal space to compress said sound transmitting medium in said chamber.

13. A scanner according to claim 12, wherein said compressing means includes compression adjusting means for adjusting a capacity of the internal space to adjust a compression pressure.

14. A scanner according to claim 13, wherein said compression adjusting means includes a first sleeve, and a second sleeve which is engaged with an outer surface of said first sleeve, and is movable with respect to said first sleeve, said first and second sleeves cooperate with each other to define said internal space which communicates with said chamber, and said elastic means is arranged so as to contact with said sound transmitting medium in said internal space, whereby said second sleeve is moved with respect to said first sleeve, so that a capacity of the internal space is changed to control the compression pressure.

15. A scanner according to claim 9, wherein said swinging means includes drive force generating means having a drive shaft for generating a drive force of swinging movement, and a link mechanism for transmitting the drive force from said drive force generating means to said transducer element, said link mechanism including (a) a first link member having a distal end and a proximal end which is fixed to said drive shaft, (b) a second link member having a distal end and a proximal end which is rotatably coupled to said distal end of said first link member, and (c) a third link member which has a proximal end rotatably coupled to said distal end of said second link member, and a distal end rotatably supported in said housing, said transducer element coupled to the third link member, whereby when said drive shaft is swung, said link members in said link mechanism are moved, so that said transducer element is swung.

16. A scanner according to claim 15, wherein said drive shaft is made of said permanent magnet having one side, in a radial direction, serving as a north pole and the other side, in the radial direction, serving as a south pole, and said drive force generating means includes, a stator having a pair of opposite surfaces arranged to sandwich said drive shaft, and coil means for periodically exciting said pair of opposite surfaces of said stator, so that said pair of opposite surfaces are periodically magnetized to north and south poles to swing said drive shaft.

17. A mechanical ultrasonic scanner, comprising:

a housing;

a transducer element swingably supported in said housing;

drive force generating means including a drive shaft for generating a drive force of swinging movement; and a link mechanism for transmitting the drive force from said drive force generating means to said transducer element, said link mechanism including (a) a first link member having a distal end and a proximal end which is fixed to said drive shaft, (b) a second link member having a distal end and a proximal end which is rotatably coupled to said distal end of said first link member, and (c) a third link member which has a proximal end rotatably coupled to said distal end of said second link member, and a distal end rotatably supported in said housing, said transducer element coupled to the third link member, whereby when said drive shaft is swung, said link members in said link mechanism are moved, so that said transducer element is swung.

18. A scanner according to claim 17, wherein said housing has a support shaft on which the distal end of the third link member is supported, and said drive and support shafts extend to be parallel to each other, and $\overline{AB}=\overline{CD}$, and $\overline{BC}=\overline{DA}$ where A is a center of said drive shaft, B is a coupling point between said first and second link members, C is a coupling point between said second and third link members, and D is a center of said support shaft.

19. A scanner according to claim 18, wherein a line which connects said point B to said point C intersects with a line which connects said point A to said point D.

20. A scanner according to claim 18, wherein a swinging center of an ultrasonic beam radiated from said transducer element coincides with a center of said support shaft.

21. A scanner according to claim 17, wherein said drive shaft is made of said permanent magnet having one side, in a radial direction, serving as a north pole and the other side, in the radial direction, serving as a south pole, and said drive force generating means includes, a stator having a pair of opposite surfaces arranged to sandwich said drive shaft, and coil means for periodically exciting said pair of opposite surfaces of said stator, so that said pair of opposite surfaces are periodically magnetized to north and south poles to swing said drive shaft.

22. A mechanical ultrasonic scanner, comprising:

a housing;

a transducer element swingably supported in said housing;

drive force generating means for generating a drive force of swinging movement; and transmitting means for transmitting the drive force to said transducer element to swing said transducer element, said drive force generating means including (a) a drive shaft made of a permanent magnet having one side, in a radial direction serving as a north pole, and the other side, in a radial direction, serving as a south pole, (b) a stator having a pair of opposite surfaces which are spaced apart from and face with surfaces of the sides of said drive shaft, said drive shaft being surrounded by the opposite surfaces of said stator and located within a space formed by the opposite surfaces of said stator, and (c) coil means for periodically exciting said pair of opposite surfaces of said stator, so that said pair of opposite surfaces are periodically magnetized to north and south poles to swing said drive shaft.

23. A scanner according to claim 22, wherein said stator includes a thin-wall portion which couples said pair of opposite surfaces to each other.

24. A scanner according to claim 22, wherein said stator includes a slit defined between said pair of opposite surfaces.

25. A scanner according to claim 24, wherein said stator includes projecting and recessed portions formed on said pair of opposite surfaces.

* * * * *